United States Patent
Nishimura et al.

(10) Patent No.: US 9,040,736 B2
(45) Date of Patent: May 26, 2015

(54) STABILIZED ISOCYANATE GROUP-CONTAINING ETHYLENICALLY UNSATURATED COMPOUND

(75) Inventors: Norihito Nishimura, Aizuwakamatsu (JP); Shinichi Yorozuya, Aizuwakamatsu (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 13/984,391

(22) PCT Filed: Feb. 2, 2012

(86) PCT No.: PCT/JP2012/052382
§ 371 (c)(1),
(2), (4) Date: Aug. 8, 2013

(87) PCT Pub. No.: WO2012/111445
PCT Pub. Date: Aug. 23, 2012

(65) Prior Publication Data
US 2013/0317248 A1 Nov. 28, 2013

(30) Foreign Application Priority Data

Feb. 15, 2011 (JP) ................................ 2011-029751

(51) Int. Cl.
*C07C 69/00* (2006.01)
*C07C 263/18* (2006.01)
*C07C 265/04* (2006.01)

(52) U.S. Cl.
CPC ............. *C07C 263/18* (2013.01); *C07C 265/04* (2013.01)

(58) Field of Classification Search
CPC .... C07C 263/18; C07C 265/04; C07C 265/05
USPC ........................................................... 560/4
See application file for complete search history.

(56) References Cited

U.S. PATENT DOCUMENTS

| | | | | |
|---|---|---|---|---|
| 3,728,369 A | * | 4/1973 | Heinert ..................... | 560/331 |
| 4,314,948 A | * | 2/1982 | Koenig et al. ............. | 560/348 |
| 2006/0229464 A1 | | 10/2006 | Morinaka et al. | |
| 2006/0241319 A1 | | 10/2006 | Morinaka et al. | |
| 2007/0197762 A1 | * | 8/2007 | Nozawa et al. ............ | 528/190 |
| 2010/0099827 A1 | | 4/2010 | Nishimura et al. | |
| 2010/0280204 A1 | | 11/2010 | Ishii | |
| 2011/0137066 A1 | | 6/2011 | Nishimura et al. | |
| 2012/0205234 A1 | | 8/2012 | Nishimura et al. | |

FOREIGN PATENT DOCUMENTS

| | | | |
|---|---|---|---|
| CN | 1829685 A | | 9/2006 |
| CN | 1829686 A | | 9/2006 |
| CN | 101910117 A | | 12/2010 |
| JP | 04109250 | * | 4/1992 |
| JP | 9-301921 A | | 11/1997 |
| JP | 2000-86612 A | | 3/2000 |
| JP | 2008-137948 A | | 6/2008 |
| JP | 2009-51785 A | | 3/2009 |
| WO | 2010/016540 A1 | | 2/2010 |

OTHER PUBLICATIONS

JP04109250 Translation 1992.*

* cited by examiner

*Primary Examiner* — Yevegeny Valenrod
*Assistant Examiner* — Blaine G Doletski
(74) *Attorney, Agent, or Firm* — Sughrue Mion, PLLC

(57) ABSTRACT

An object of the present invention is to improve the stability of an ethylenically unsaturated compound having an isocyanate group in the molecule by preventing a polymerization of the ethylenically unsaturated compound. The present invention relates to a stabilizing composition for an isocyanate group-containing ethylenically unsaturated compound, comprising: an isocyanate group-containing ethylenically unsaturated compound (A) which comprises one or more isocyanate groups and one or more ethylenically unsaturated groups in the molecule; and a stabilizing agent (B) which is a compound in which at least one of the ethylenically unsaturated groups in the compound (A) is replaced with an alkyl group which may have a substituent.

7 Claims, No Drawings

STABILIZED ISOCYANATE GROUP-CONTAINING ETHYLENICALLY UNSATURATED COMPOUND

CROSS REFERENCE TO RELATED APPLICATIONS

This application is a National Stage of International Application No. PCT/JP2012/052382 filed Feb. 2, 2012 (claiming priority based on Japanese Patent Application No. 2011-029751 filed Feb. 15, 2011), the contents of which are incorporated herein by reference in their entirety.

TECHNICAL FIELD

The present invention relates to a stabilized isocyanate group-containing ethylenically unsaturated compound and more specifically relates to a stabilizing composition containing the compound and to a method for producing the compound.

BACKGROUND ART

Since an ethylenically unsaturated compound is prone to be extremely polymerized by heat, light and other factors, a solid is often generated by polymerization in the steps of producing and purifying an ethylenically unsaturated compound and causes the failure of production facilities. When the solid adheres to a production tank, a distillation column, a pipe and the like in the steps of producing and purifying an ethylenically unsaturated compound, not only, e.g., clogging due to the solid and anchoring of mobile facilities occur but also the solid interferes with the production and purification of the ethylenically unsaturated compound. In addition, the removal of the solid adhering to related facilities is generally performed by operation by human power and therefore has poor operation efficiency, a long-term shutdown is thus unavoidable, and an economic loss is large. Also, the deterioration of product quality is also caused.

Although it is known that the addition of various solid polymerization inhibitors is effective as a method for preventing the polymerization of an ethylenically unsaturated compound, only the addition is insufficient and many polymerization preventing methods other than the method have been proposed or performed.

For example, there has been proposed a method of adding a compound, in which Michael addition of alcohol or (meth)acrylic acid to a (meth)acrylic acid ester occurs, in a low-boiling point impurity distilling step of a crude (meth)acrylic acid ester (Patent Literature 1). However, this method is less effective since alcohol in a Michael addition moiety is desorbed by heating to reproduce a (meth)acrylic group in the case of using the Michael adduct of an alcohol or is ineffective from the viewpoint of the prevention of polymerization since there is still a (meth)acrylic group which is polymerizable in the case of using the compound in which the Michael addition of (meth)acrylic acid occurs. Furthermore, the addition of various impurities having such different strictures is not preferred since a functionally adverse effect is caused when using the product to make a secondary product (such as a resin molding, a coating or an optical material).

In view of the above, the advent of a method for more effectively preventing the polymerization of an ethylenically unsaturated compound has been earnestly desired.

CITATION LIST

Patent Literature

Patent Literature 1: JP-H9(1997)-301921 A

SUMMARY Of INVENTION

Technical Problem

In view of the conventional problems, an object of the present invention is to improve the stability of an ethylenically unsaturated compound having an isocyanate group in the molecule by preventing a polymerization of the ethylenically unsaturated compound.

Solution to Problem

As a result of performing extensive research in order to solve the problems, the present inventors found that an isocyanate group-containing ethylenically unsaturated compound is stabilized by incorporating a certain stabilizing agent into the isocyanate group-containing ethylenically unsaturated compound, and the present invention was thus accomplished. The present invention includes, e.g., the following sections.

[1] A stabilizing composition for an isocyanate group-containing ethylenically unsaturated compound, comprising: an isocyanate group-containing ethylenically unsaturated compound (A) which comprises one or more isocyanate groups and one or more ethylenically unsaturated groups in the molecule; and a stabilizing agent (B) which is a compound in which at least one of the ethylenically unsaturated groups in the compound (A) is replaced with an alkyl group which may have a substituent.

[2] The stabilizing composition according to the section [1], wherein the compound (A) is a compound comprising one or more ethylenically unsaturated groups represented by the following formula (1); and the stabilizing agent (B) is a compound in which at least one of the ethylenically unsaturated groups represented by the formula (1) in the compound (A) is replaced with a structure represented by the following formula (2) or (3):

(wherein $R^1$ to $R^3$ each independently represent a hydrogen atom, an alkyl group having 1 to 4 carbon atoms or an aromatic group);

(wherein $R^4$ to $R^8$ each independently represent a hydrogen atom, an alkyl group having 1 to 4 carbon atoms or an aromatic group);

(wherein $R^9$ to $R^{11}$ each independently represent a hydrogen atom or an aromatic group).

[3] The stabilizing composition according to the section [1] or [2], comprising the stabilizing agent (B) in an amount of 0.005% by mass to 5% by mass.

[4] The stabilizing composition according to any of the sections [1] to [3], wherein the compound (A) is a compound comprising one or more groups represented by the following formula (4):

(wherein $R^1$ to $R^3$ each independently represent a hydrogen atom, an alkyl group having 1 to 4 carbon atoms or an aromatic group).

[5] The stabilizing composition according to any of the sections [1] to [4], wherein the compound (A) is a compound represented by the following formula (5):

$$CR^2R^3\!=\!CR^1\!-\!(CO)\!-\!O\!-\!R^{12}\!-\!NCO \quad (5)$$

(wherein $R^1$ to $R^3$ each independently represent a hydrogen atom, an alkyl group having 1 to 4 carbon atoms or an aromatic group; and $R^{12}$ represents a straight or branched chain alkylene group having 1 to 10 carbon atoms or $-R^{13}PhR^{14}-$ ($R^{13}$ and $R^{14}$ represent a single bond or an alkylene group having 1 to 3 carbon atoms; and Ph represents a phenylene group)).

[6] The stabilizing composition according to any of the sections [1] to [5], wherein the compound (A) is 2-acryloyloxyethyl isocyanate, 2-methacryloyloxyethyl isocyanate, 1,1-(bisacryloyloxymethyl)ethyl isocyanate or 2-(isocyanatoethyloxy)ethyl methacrylate.

[7] The stabilizing composition according to any of the sections [1] to [6], wherein the compound (A) is 2-acryloyloxyethyl isocyanate and the stabilizing agent (B) is at least one compound selected from the group consisting of 2-n-propionyloxyethyl isocyanate and 2-acetoxyethyl isocyanate.

[8] The stabilizing composition according to any of the sections [1] to [6], wherein the compound (A) is 2-methacryloyloxyethyl isocyanate and the stabilizing agent (B) is at least one compound selected from the group consisting of 2-isobutyroyloxyethyl isocyanate and 2-n-propionyloxyethyl isocyanate.

[9] A method for producing a stabilized isocyanate group-containing ethylenically unsaturated compound, wherein, in a process for producing an isocyanate group-containing ethylenically unsaturated compound (A) which comprises one or more isocyanate groups and one or more ethylenically unsaturated groups in the molecule, a precursor for a stabilizing agent (B) is incorporated into a raw material for producing the compound (A) to generate the stabilizing agent (B) in the process; and the stabilizing agent (B) is a compound in which at least one of the ethylenically unsaturated groups in the compound (A) is replaced with an alkyl group which may have a substituent.

[10] A method for producing a stabilized isocyanate group-containing ethylenically unsaturated compound, wherein, in a process for producing an isocyanate group-containing ethylenically unsaturated compound (A) which comprises one or more isocyanate groups and one or more ethylenically unsaturated groups in the molecule, a stabilizing agent (B) is incorporated into a raw material for producing the compound (A); and the stabilizing agent (B) is a compound in which at least one of the ethylenically unsaturated groups in the compound (A) is replaced with an alkyl group which may have a substituent.

[11] A method for producing a stabilized isocyanate group-containing ethylenically unsaturated compound, wherein, in a process for producing an isocyanate group-containing ethylenically unsaturated compound (A) which comprises one or more isocyanate groups and one or more ethylenically unsaturated groups in the molecule, a stabilizing agent (B) is added to the compound (A); and the stabilizing agent (B) is a compound in which at least one of the ethylenically unsaturated groups in the compound (A) is replaced with an alkyl group which may have a substituent.

Effect of the Invention

In accordance with the present invention, an isocyanate group-containing ethylenically unsaturated compound can be effectively stabilized. Thus, there can be effectively prevented the generation of impurities in production, product storage or the like; the generation of a solid, the occurrence of cloudiness, discoloration and reduction in purity due to polymerization; and the like.

EMBODIMENT FOR CARRYING OUT THE INVENTION

The present invention relates to a stabilizing composition comprising a stabilized isocyanate group-containing ethylenically unsaturated compound and to a method for producing the compound. The present invention will be described in detail below.

As used herein, "ethylenically unsaturated compound" means a compound having at least one ethylenically unsaturated group in the molecule, and the ethylenically unsaturated group may have a substituent. "(Meth)acryloyl" means acryloyl or methacryloyl and also encompasses groups of which some of the hydrogen atoms are substituted. Further, hydrolyzable chlorine is an organic or inorganic chlorine compound that is generated during producing isocyanate and reacts with methanol to generate hydrogen chloride under the test conditions according to Japanese Industrial Standard JIS K1603-3: 2007 and is contained as an impurity in an isocyanate group-containing ethylenically unsaturated compound.

[Stabilizing Composition]

The stabilizing composition according to the present invention comprises an isocyanate group-containing ethylenically unsaturated compound (A) and a stabilizing agent (B).

<Isocyanate Group-Containing Ethylenically Unsaturated Compound (A)>

The isocyanate group-containing ethylenically unsaturated compound (A) comprises one or more isocyanate groups and one or more ethylenically unsaturated groups in the molecule, and a hydrogen atom in the ethylenically unsaturated groups may be substituted.

The compound (A) is preferably a compound comprising one or more ethylenically unsaturated groups represented by the following formula (1).

$$-CR^1\!=\!CR^2R^3 \quad (1)$$

In the formula (1), $R^1$ to $R^3$ each independently represent a hydrogen atom, an alkyl group having 1 to 4 carbon atoms or an aromatic group. The alkyl group and the aromatic group may also be substituted by a fluorine atom. From the viewpoint of the availability of a raw material and reactivity in the use of the compound (A) for a subsequent polymerization reaction, it is preferable that $R^1$ to $R^3$ are each independently a hydrogen atom, a methyl group or an ethyl group, and it is more preferable that $R^1$ is a hydrogen atom or a methyl group and $R^2$ and $R^3$ are hydrogen atoms.

The compound (A) is more preferably a compound comprising one or more groups having an ester bond and an ethylenically unsaturated group, represented by the following formula (4).

$$-O\!-\!(CO)\!-\!CR^1\!=\!CR^2R^3 \quad (4)$$

In the formula (4), $R^1$ to $R^3$ represent the same meanings as $R^1$ to $R^3$ in the formula (1).

The compound (A) is further preferably a compound represented by the following formula (5).

$$CR^2R^3\!=\!CR^1\!-\!(CO)\!-\!O\!-\!R^{12}\!-\!NCO \quad (5)$$

In the formula (5), $R^1$ to $R^3$ represent the same meanings as $R^1$ to $R^3$ in the formula (1); and $R^{12}$ represents a straight or branched chain alkylene group having 1 to 10 carbon atoms or —$R^{13}PhR^{14}$— ($R^{13}$ and $R^{14}$ represent a single bond or an alkylene group having 1 to 3 carbon atoms and Ph represents a phenylene group), preferably a straight or branched chain alkylene group having 2 to 6 carbon atoms or a phenylene group, wherein the alkylene group and the phenylene group may be substituted by a fluorine atom.

In a preferred embodiment of the formula (5), $R^1$ is a hydrogen atom or a methyl group; $R^2$ and $R^3$ are each independently a hydrogen atom, a methyl group or an ethyl group; and $R^{12}$ is a straight or branched chain alkylene group having 2 to 6 carbon atoms or a phenylene group.

Examples of the compound (A) include, but are not limited to, 2-methacryloyloxyethyl isocyanate, 3-methacryloyloxy-n-propyl isocyanate, 2-methacryloyloxyisopropyl isocyanate, 4-methacryloyloxy-n-butyl isocyanate, 2-methacryloyloxy-tert-butyl isocyanate, 2-methacryloyloxybutyl-4-isocyanate, 2-methacryloyloxybutyl-3-isocyanate, 2-methacryloyloxybutyl-2-isocyanate, 2-methacryloyloxybutyl-1-isocyanate, 5-methacryloyloxy-n-pentyl isocyanate, 6-methacryloyloxy-n-hexyl isocyanate, 7-methacryloyloxy-n-heptyl isocyanate, 2-(isocyanatoethyloxy)ethyl methacrylate, 3-methacryloyloxyphenyl isocyanate, 4-methacryloyloxyphenyl isocyanate, 2-acryloyloxyethyl isocyanate, 3-acryloyloxy-n-propyl isocyanate, 2-acryloyloxyisopropyl isocyanate, 4-acryloyloxy-n-butyl isocyanate, 2-acryloyloxy-tert-butyl isocyanate, 2-acryloyloxybutyl-4-isocyanate, 2-acryloyloxybutyl-3-isocyanate, 2-acryloyloxybutyl-2-isocyanate, 2-acryloyloxybutyl-1-isocyanate, 5-acryloyloxy-n-pentyl isocyanate, 6-acryloyloxy-n-hexyl isocyanate, 7-acryloyloxy-n-heptyl isocyanate, 2-(isocyanatoethyloxy)ethyl acrylate, 3-acryloyloxyphenyl isocyanate, 4-acryloyloxyphenyl isocyanate, 1,1-bis(methacryloyloxymethyl)methyl isocyanate, 1,1-bis(methacryloyloxymethyl)ethyl isocyanate, 1,1-bis(acryloyloxymethyl)methyl isocyanate, 1,1-bis(acryloyloxymethyl)ethyl isocyanate, 2'-pentenoyl-4-oxyphenyl isocyanate, compounds in which a hydrogen atom in an alkyl group in these compounds is substituted by a fluorine atom, and the like. Of these, 2-methacryloyloxyethyl isocyanate, 4-methacryloyloxy-n-butyl isocyanate, 5-methacryloyloxy-n-pentyl isocyanate, 6-methacryloyloxy-n-hexyl isocyanate, 2-acryloyloxyethyl isocyanate, 3-methacryloyloxyphenyl isocyanate, 4-methacryloyloxyphenyl isocyanate, 1,1-bis(methacryloyloxymethyl)ethyl isocyanate, 2-(isocyanatoethyloxy)ethyl methacrylate, and 2-(isocyanatoethyloxy)ethyl acrylate are preferred from the viewpoint of the availability of a raw material.

<Stabilizing Agent (B)>

The stabilizing agent (B) according to the present invention is a compound having the same structure as that of the compound (A), except that at least one of the ethylenically unsaturated groups in the compound (A) to be stabilized is replaced with an alkyl group which may have a substituent. The alkyl group which may have a substituent may be a straight- or branched-chain alkyl group, preferably having 1 to 10 carbon atoms, more preferably having 1 to 4 carbon atoms. The alkyl group may have a substituent but preferably has no substituent.

When the compound (A) is a compound comprising one or more ethylenically unsaturated groups represented by the formula (1), the stabilizing agent (B) is preferably a compound in which at least one of the ethylenically unsaturated groups represented by the formula (1) in the compound (A) is replaced with a structure represented by the following formula (2) or (3).

In the formulae (2) and (3), $R^4$ to $R^8$ each independently represent a hydrogen atom, an alkyl group having 1 to 4 carbon atoms or an aromatic group; $R^9$ to $R^{11}$ each independently represent a hydrogen atom or an aromatic group; and the alkyl group having 1 to 4 carbon atoms and the aromatic group may be substituted by a fluorine atom.

In the formula (2), it is preferable that any one of $R^4$ and $R^5$ has the same structure as that of $R^1$ in the formula (1) and any two of $R^6$ to $R^8$ have the same structures as those of $R^2$ and $R^3$. Further, it is more preferable that any one of $R^4$ and $R^5$ has the same structure as that of $R^1$ in the formula (1) and any two of $R^6$ to $R^8$ have the same structures as those of $R^2$ and $R^3$ and the remainder is a hydrogen atom.

In the formula (3), it is preferable that $R^9$ to $R^{11}$ are hydrogen atoms or have the same structures as those of $R^1$ to $R^3$ in the formula (1) and it is more preferable that any one of $R^9$ to $R^{11}$ has the same structure as that of $R^1$ in the formula (1) and the two remainders are hydrogen atoms.

In accordance with a preferred embodiment of the compound (A), the stabilizing agent (B) is more preferably a compound comprising one or more groups represented by the following formula (6) or (7), further preferably a compound represented by the following formula (8) or (9).

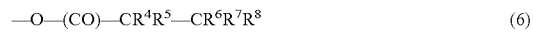

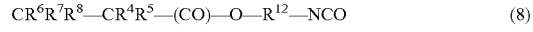

In the formulae (6) to (9), $R^4$ to $R^8$ represent the same meanings as those of $R^4$ to $R^8$ in the formula (2); $R^9$ to $R^{11}$ represent the same meanings as those of $R^9$ to $R^{11}$ in the formula (3); and $R^{12}$ represents the same meaning as that of $R^{12}$ in the formula (5).

Examples of the stabilizing agent (B) include, but are not limited to, 2-n-propionyloxyethyl isocyanate, 4-n-butanoyloxyphenyl isocyanate, 2-isobutyroyloxyethyl isocyanate, 4-n-pentanoyloxyphenyl isocyanate, 2'-methyl-n-butanoyl-4-oxyphenyl isocyanate, acetoxyethyl isocyanate, 4-acetoxyphenyl isocyanate and the like.

<Content of Stabilizing Agent (B)>

The content of the stabilizing agent (B) in the stabilizing composition of the present invention is preferably 0.005% by mass or more and 5% by mass or less, more preferably 0.1% by mass or more and 3% by mass or less. The content of less than 0.005% by mass may cause a sufficient stabilization effect to be prevented from being expressed while the case of the content of more than 5% by mass is not preferred in terms of economical efficiency.

<Constitution Examples>

Examples of combinations of the compound (A) and the stabilizing agent (B) include, but are not limited to:

a combination of 2-acryloyloxyethyl isocyanate as the compound (A) and at least one compound selected from 2-n-propionyloxyethyl isocyanate and acetoxyethyl isocyanate as the stabilizing agent (B);

a combination of 2-methacryloyloxyethyl isocyanate as the compound (A) and at least one compound selected from 2-isobutyroyloxyethyl isocyanate and 2-n-propionyloxyethyl isocyanate as the stabilizing agent (B);

a combination of 2'-pentenoyl-4-oxyphenyl isocyanate as the compound (A) and at least one compound selected from 4-n-pentanoyloxyphenyl isocyanate, 2'-methyl-n-butanoyl- 4-oxyphenyl isocyanate, 4-n-butanoyloxyphenyl isocyanate and 4-acetoxyphenyl isocyanate as the stabilizing agent (B); and the like.

<Another Component>

The stabilizing composition of the present invention may comprise a common polymerization inhibitor. Examples of the polymerization inhibitor include: phenolic polymerization inhibitors such as 2,6-di-t-butyl-4-methylphenol and quinone; sulfur-based polymerization inhibitors such as phenothiazine; phosphorus-based polymerization inhibitors; N-oxyl compounds such as 4-hydroxy-2,2,6,6-tetramethylpiperidinoxyl free radical; and the like.

<Polymerization>

As used herein, "polymerization" encompasses the generation of a solid (in popcorn, glass or gel form), such as the generation of, e.g., a granular or massive solid as a polymer or the solidification of a liquid phase portion as well as the state in which a compound of which the multimerization or oligomerization occurs due to the polymerization reaction of the compound (A) is not generated as a solid but is dissolved in the liquid of the compound (A). Such a case can be confirmed by quantitating the decrease amount of the compound (A) or the production amount of an oligomer by a common analytical method (e.g., gas chromatography, high performance liquid chromatography or the like).

[Method for Producing Stabilized Isocyanate Group-Containing Ethylenically Unsaturated Compound]

Examples of the method for obtaining a stabilizing composition comprising the compound (A) and the stabilizing agent (B) (method for producing a stabilized isocyanate group-containing ethylenically unsaturated compound) include, but are not limited to:

i) a method of adding a separately synthesized stabilizing agent (B) to a compound (A) or recycling a stabilizing agent (B) collected in a process for producing a compound (A) to add it to a compound (A);

ii) a method of incorporating a stabilizing agent (B) into a raw material for producing a compound (A) or a method of incorporating a precursor for a stabilizing agent (B) into a raw material for producing a compound (A) and making a reaction proceed with the raw material to generate a stabilizing agent (B), in the process for producing a compound (A); and the like.

The precursor is not particularly limited as long as the precursor is a compound that is finally converted into a stabilizing agent (B) when being subjected to a reaction by being incorporated into a raw material for a compound (A) in a process for producing a compound (A). When the raw material for a compound (A) is a compound comprising one or more ethylenically unsaturated groups represented by the formula (1), examples of the precursor for a stabilizing agent (B) include: a compound in which at least one of the ethylenically unsaturated groups represented by the formula (1) in the raw material for the compound (A) is replaced with a structure represented by the formula (2) or (3); and the like.

Specific examples of i) as described above include a method of adding separately synthesized and purified 2-n-propionyloxyethyl isocyanate to 2-acryloyloxyethyl isocyanate before or after distillation.

Specific examples of ii) as described above include: a method of incorporating 2-n-propionyloxyethyl isocyanate functioning as a stabilizing agent into a final product by incorporating a specific amount of propionic acid into acrylic acid as a raw material to perform the reaction thereof when acrylic acid is reacted with phosgene to produce 3-chloropropionic acid chloride, which is reacted with ethanolamine hydrochloride to obtain 3'-chloropropionyl-2-oxyethylamine hydrochloride, followed by producing 2-acryloyloxyethyl isocyanate by the steps of isocyanation and dechlorination of amine; and the like.

<Mechanism of Stabilization>

The following points are considered as characteristics contributing to the mechanism of stabilizing the compound (A) according to the present invention.

By blending the compound (A) with the stabilizing agent (B) having the structure in which at least one of the ethylenically unsaturated groups in the compound (A) is replaced with an alkyl group, destabilization such as polymerization is suppressed since an overall double bond equivalent is decreased or the stabilizing agent (B) receives a generated heat radical. Further, examples of the points include such an advantage that the physical properties of a coating film or the like during use thereof as a resin composition or after curing are not adversely affected since the structures of the compound (A) and the stabilizing agent (B) are similar.

EXAMPLES

The present invention will be described below based on examples but the present invention is not limited to these examples.

[Stabilization of Isocyanate Group-Containing Ethylenically Unsaturated Compound on Presumption of Heating Reaction Conditions]

Example 1

(1-1) Synthesis of 2-acryloyloxyethyl isocyanate reaction liquid (Step 1)

In a four-neck flask equipped with a thermometer, a cooling pipe, a gas supply pipe and a stirring apparatus, 200 g of acrylic acid and 4 g of dimethylformamide were put and heated to 70° C., and 400 g of phosgene was supplied for 40 hours. After the supply, excess phosgene was removed, followed by distilling off the resultant under reduced pressure (60° C./3 kPa). There was separated 20 g of the first fraction, and 200 g of 3-chloropropionic acid chloride was obtained as a main fraction.

(Step 2)

In a four-neck flask equipped with a thermometer, a cooling pipe, a gas supply pipe and a stirring apparatus, 750 mL of toluene and 75 g (1.23 mol) of ethanolamine were put and heated to 90° C., and about 60 g of hydrogen chloride gas was supplied. Then, 177 g (1.39 mol) of 3-chloropropionic acid chloride obtained in the step 1 was dropwise added for 270 minutes and heated at 90° C. for 1 hour. Thereafter, 240 g (2.43 mol) of phosgene was supplied for 12 hours. Then, dissolved phosgene and toluene were removed to obtain 241 g (content of 81.0% by mass by gas chromatography, 1.10 mol as purity) of a 3-chloropropionic acid (2-isocyanatoethyl) ester reaction liquid.

(Step 3)

In a three-necked flask, 670 mL of toluene, 241 g (1.10 mol) of the 3-chloropropionic acid (2-isocyanatoethyl) ester reaction liquid obtained in the step 2, and 134 g (1.31 mol) of triethylamine (boiling point; 89.4° C.) were put, and heated and stirred at 50° C. for 6 hours. After stirring, the resultant was cooled to room temperature, and generated triethylamine hydrochloride was filtrated. Then, excess triethylamine and toluene were distilled off to obtain 183 g of a reaction liquid of 2-acryloyloxyethyl isocyanate (concentration of 78.8% by mass by gas chromatography, 1.02 mol as purity).

(1-2) Stabilization of 2-acryloyloxyethyl isocyanate reaction liquid

In a glass flask with a capacity of 300 mL, including a cooling condenser (which had an outlet opened at atmospheric pressure and was equipped with a granular calcium chloride pipe) and a thermometer, 127 g of the reaction liquid of 2-acryloyloxyethyl isocyanate (hereinafter also referred to as "AOI monomer") (78.8% as purity, the content of 2-acryloyloxyethyl isocyanate by gas chromatograph was 100 g) as the isocyanate group-containing ethylenically unsaturated compound (A) and 1 g of 2-n-propionyloxyethyl isocyanate as the stabilizing agent (B) were put and heated in an oil bath at 100° C. for 8 hours. When the amount of a remaining AOI monomer was quantitated by gas chromatography after finishing the heating, the amount was decreased by about 0.4% based on the loading amount. In this case, the appearance of the internal liquid in the flask was transparent without change.
<Analytical Conditions>
Column: J & W Co., DB-1 (length of 30 m, inner diameter of 0.32 mm, film thickness of 1 μm)
Sample injector temperature: 300° C.
Detector temperature: 300° C.
Detector: FID (hydrogen flame type detector)
Temperature-raising program: 50° C.→10° C./min→320° C. (5 min hold)
Flow rate: 1.2 mL/min
Sample dilution solvent: methylene chloride Comparative Example 1

The amount of a remaining AOI monomer was evaluated by the same method as in Example 1 except that 2-n-propionyloxyethyl isocyanate was not used. As a result, the amount was decreased by about 7.3% based on the loading amount. In this case, white fine particles were generated and floated in the internal liquid in the flask.

Example 2

(2-1) Synthesis of 2-acryloyloxyethyl isocyanate reaction liquid containing 2-n-propionyloxyethyl isocyanate By the same method as in Example 1 except that a mixture of 1 g of propionic acid with 199 g of acrylic acid was used instead of 200 g of acrylic acid in the step 1 of Example 1, 183 g of a reaction liquid of 2-acryloyloxyethyl isocyanate was obtained. In analysis by gas chromatography, 2-acryloyloxyethyl isocyanate in a content of 77.9% by mass and 1.01 mol as purity and 2-n-propionyloxyethyl isocyanate in 0.7% by mass and 0.01 mol as purity were contained.

(2-2) Evaluation of stability of 2-acryloyloxyethyl isocyanate reaction liquid

Since the 2-acryloyloxyethyl isocyanate reaction liquid synthesized in (2-1) as described above had already contained 2-n-propionyloxyethyl isocyanate as the stabilizing agent (B), the amount of a remaining AOI monomer was evaluated by the same method as in Example 1 using 130 g of the reaction liquid (the content of the compound (A) of 101 g and the content of the stabilizing agent (B) of 0.9 g). As a result, the amount of AOI was decreased by about 0.7% based on the loading amount. In this case, no change of the appearance was seen.

Example 3

The amount of a remaining AOI monomer was evaluated by the same method as in (1-2) of Example 1 except that 100 g of 2-acryloyloxyethyl isocyanate ("KarenzAOI" (registered trademark) manufactured by Showa Denko K.K., purity of 99.7% by gas chromatography) was used instead of 127 g of the AOI monomer reaction liquid as the isocyanate group-containing ethylenically unsaturated compound (A). As a result, the amount was decreased by 0.3% based on the loading amount. In this case, no change of the appearance was seen.

Comparative Example 2

The amount of a remaining AOI monomer was evaluated by the same method as in Example 3 except that 2-n-propionyloxyethyl isocyanate was not used. As a result, the amount was decreased by about 2.3% based on the loading amount. In this case, white fine particles were generated in the internal liquid in the flask.

Example 4

The amount of a remaining MOI monomer was evaluated by the same method as in (1-2) of Example 1 except that 100 g of 2-methacryloyloxyethyl isocyanate ("KarenzMOI" (registered trademark) manufactured by Showa Denko K.K., purity of 99.7% by gas chromatography, hereinafter also referred to as "MOI monomer") was used instead of 127 g of the AOI monomer reaction liquid as the isocyanate group-containing ethylenically unsaturated compound (A). As a result, the amount was decreased by about 0.6% based on the loading amount. In this case, no change of the appearance was seen.

Comparative Example 3

The amount of a remaining MOI monomer was evaluated by the same method as in Example 4 except that 2-n-propionyloxyethyl isocyanate was not used. As a result, the amount was decreased by about 3.2% based on the loading amount. In this case, white fine particles were generated in the internal liquid in the flask.

Example 5

The amount of a remaining MOI monomer was evaluated by the same method as in (1-2) of Example 1 except that 100 g of an MOI monomer was used instead of 127 g of the AOI monomer reaction liquid as the isocyanate group-containing ethylenically unsaturated compound (A) and 1 g of 2-isobutyroyloxyethyl isocyanate was used instead of 1 g of 2-n-propionyloxyethyl isocyanate as the stabilizing agent (B). As a result, the amount was decreased by 0.5% based on the loading amount. In this case, no change of the appearance was seen.

Comparative Example 4

The amount of a remaining MOI monomer was evaluated by the same method as in Example 5 except that 2-isobutyroyloxyethyl isocyanate was not used. As a result, the amount was decreased by about 3.3% based on the loading amount. In this case, white fine particles were generated in the internal liquid in the flask.

Example 6

The amount of a remaining MOI monomer was evaluated by the same method as in (1-2) of Example 1 except that 100 g of an MOI monomer was used instead of 127 g of the AOI monomer reaction liquid as the isocyanate group-containing ethylenically unsaturated compound (A) and 1 g of acetoxyethyl isocyanate was used instead of 1 g of 2-n-propionyloxyethyl isocyanate as the stabilizing agent (B). As a result, the amount was decreased by 0.2% based on the loading amount. In this case, no change of the appearance was seen.

Comparative Example 5

The amount of a remaining MOI monomer was evaluated by the same method as in Example 6 except that acetoxyethyl isocyanate was not used. As a result, the amount was decreased by about 3.0% based on the loading amount. In this case, white fine particles were generated in the internal liquid in the flask.

The invention claimed is:

1. A stabilizing composition for an isocyanate group-containing ethylenically unsaturated compound, comprising:
   an isocyanate group-containing ethylenically unsaturated compound (A) which comprises one or more isocyanate groups and one or more ethylenically unsaturated groups represented by following formula (1); and
   a stabilizing agent (B) which is a compound having the same structure as compound (A) except that at least one of the ethylenically unsaturated groups represented by formula (1) in the compound (A) is replaced with a structure represented by following formula (2) or (3):

$$-CR^1{=}CR^2R^3 \quad (1)$$

wherein $R^1$ to $R^3$ each independently represent a hydrogen atom, an alkyl group having 1 to 4 carbon atoms or an aromatic group;

$$-CR^4R^5{-}CR^6R^7R^8 \quad (2)$$

wherein $R^4$ to $R^8$ each independently represent a hydrogen atom, an alkyl group having 1 to 4 carbon atoms or an aromatic group;

$$-CR^9R^{10}R^{11} \quad (3)$$

wherein $R^9$ to $R^{11}$ each independently represent a hydrogen atom or an aromatic group; and
   wherein none of $R^1$ to $R^{11}$ includes a substituent.

2. The stabilizing composition according to claim 1, comprising the stabilizing agent (B) in an amount of 0.005% by mass to 5% by mass.

3. The stabilizing composition according to claim 1, wherein the compound (A) is a compound comprising one or more groups represented by the following formula (4):

$$-O{-}(CO){-}CR^1{=}CR^2R^3 \quad (4),$$

wherein $R^1$ to $R^3$ each independently represent a hydrogen atom, an alkyl group having 1 to 4 carbon atoms or an aromatic group, and wherein none of $R^1$ to $R^3$ includes a substituent.

4. The stabilizing composition according to claim 1, wherein the compound (A) is a compound represented by the following formula (5):

$$CR^2R^3{=}CR^1{-}(CO){-}O{-}R^{12}{-}NCO \quad (5),$$

wherein $R^1$ to $R^3$ each independently represent a hydrogen atom, an alkyl group having 1 to 4 carbon atoms or an aromatic group, and none of $R^1$ to $R^3$ includes a substituent; and $R^{12}$ represents a straight or branched chain alkylene group having 1 to 10 carbon atoms or $-R^{13}PhR^{14}-$ ($R^{13}$ and $R^{14}$ represent a single bond or an alkylene group having 1 to 3 carbon atoms; and Ph represents a phenylene group.

5. The stabilizing composition according to claim 1, wherein the compound (A) is 2-acryloyloxyethyl isocyanate, 2-methacryloyloxyethyl isocyanate, 1,1-(bisacryloyloxymethyl)ethyl isocyanate or 2-(isocyanatoethyloxy)ethyl methacrylate.

6. The stabilizing composition according to claim 1, wherein the compound (A) is 2-acryloyloxyethyl isocyanate and the stabilizing agent (B) is at least one compound selected from the group consisting of 2-n-propionyloxyethyl isocyanate and 2-acetoxyethyl isocyanate.

7. The stabilizing composition according to claim 1, wherein the compound (A) is 2-methacryloyloxyethyl isocyanate and the stabilizing agent (B) is at least one compound selected from the group consisting of 2-isobutyroyloxyethyl isocyanate and 2-n-propionyloxyethyl isocyanate.

* * * * *

UNITED STATES PATENT AND TRADEMARK OFFICE
CERTIFICATE OF CORRECTION

PATENT NO. : 9,040,736 B2  
APPLICATION NO. : 13/984391  
DATED : May 26, 2015  
INVENTOR(S) : Norihito Nishimura and Shinichi Yorozuya Page 1 of 1

It is certified that error appears in the above-identified patent and that said Letters Patent is hereby corrected as shown below:

In the Claims:

Column 12, Line 27: In Claim 4, delete "($R^{13}$ and $R^{14}$" and insert --$R^{13}$ and $R^{14}$--

Signed and Sealed this
Twenty-fourth Day of November, 2015

Michelle K. Lee
*Director of the United States Patent and Trademark Office*